(12) United States Patent
Surti (10) Patent No.: US 9,155,532 B2
(45) Date of Patent: Oct. 13, 2015

(54) MEDICAL DEVICES, SYSTEMS AND METHODS FOR CLOSING PERFORATIONS

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1941 days.

(21) Appl. No.: 12/125,475

(22) Filed: May 22, 2008

(65) Prior Publication Data
US 2008/0294001 A1 Nov. 27, 2008

Related U.S. Application Data

(60) Provisional application No. 60/940,246, filed on May 25, 2007.

(51) Int. Cl.
| | |
|---|---|
| *A61B 1/00* | (2006.01) |
| *A61B 1/04* | (2006.01) |
| *A61B 17/10* | (2006.01) |
| *A61B 18/18* | (2006.01) |
| *A61B 17/04* | (2006.01) |
| *A61B 17/00* | (2006.01) |

(52) U.S. Cl.
CPC ......... *A61B 17/0469* (2013.01); *A61B 17/0057* (2013.01); *A61B 17/0401* (2013.01); *A61B 17/0482* (2013.01); *A61B 2017/00637* (2013.01); *A61B 2017/00663* (2013.01); *A61B 2017/0472* (2013.01)

(58) Field of Classification Search
USPC ......... 600/104, 106, 107, 114–116, 127–130; 606/41, 138–150
See application file for complete search history.

(56) References Cited

U.S. PATENT DOCUMENTS

| | | | |
|---|---|---|---|
| 2,199,025 | A | 4/1940 | Conn |
| 3,556,079 | A | 1/1971 | Omizo |
| 4,235,238 | A | 11/1980 | Ogiu et al. |
| 5,123,914 | A | 6/1992 | Cope |

(Continued)

FOREIGN PATENT DOCUMENTS

| | | | | |
|---|---|---|---|---|
| EP | 1 762 185 | | 3/2007 | |
| JP | 2005261857 A | * | 9/2005 | ............... A61B 1/00 |

(Continued)

OTHER PUBLICATIONS

International Search Report; PCT/US2008/064508 (Aug. 29, 2008).

(Continued)

*Primary Examiner* — Ryan Henderson
(74) *Attorney, Agent, or Firm* — Brinks Gilson & Lione (57) ABSTRACT

Medical devices, systems and methods for placing tissue fixation devices are provided. The medical device includes a plurality of elongate delivery devices, a plurality of elongate tubes, and a distal tip. Each delivery device defines a delivery lumen sized to receive a tissue fixation device. Each elongate tube defines a tube lumen sized to receive one of the delivery devices. Each tube lumen has a distal port. The distal tip is connected to the plurality of elongate tubes and defines a guide surface positioned distally of the distal ports. The guide surface is structured to redirect the plurality of delivery devices radially outwardly as the plurality of delivery devices are distally translated through the tube lumens and the distal ports of the plurality of elongate tubes. A medical system is formed by an endoscope that is selectively attachable to the medical device.

19 Claims, 7 Drawing Sheets

(56) References Cited

U.S. PATENT DOCUMENTS

| | | | |
|---|---|---|---|
| 5,203,787 A | 4/1993 | Noblitt et al. | |
| 5,333,624 A | 8/1994 | Tovey | |
| 5,354,279 A * | 10/1994 | Hofling | 604/164.12 |
| 5,366,480 A | 11/1994 | Corriveau et al. | |
| 5,417,691 A | 5/1995 | Hayhurst | |
| 5,520,700 A | 5/1996 | Beyar et al. | |
| 5,527,343 A | 6/1996 | Bonutti | |
| 5,554,183 A | 9/1996 | Nazari | |
| 5,690,656 A | 11/1997 | Cope et al. | |
| 5,728,124 A | 3/1998 | Cockburn et al. | |
| 5,807,304 A | 9/1998 | Cockburn | |
| 5,810,848 A | 9/1998 | Hayhurst | |
| 5,865,791 A | 2/1999 | Whayne et al. | |
| 5,891,159 A | 4/1999 | Sherman et al. | |
| 5,908,428 A | 6/1999 | Scirica et al. | |
| 6,053,871 A | 4/2000 | Cockburn | |
| 6,110,183 A | 8/2000 | Cope | |
| RE36,974 E | 11/2000 | Bonutti | |
| 6,251,084 B1 * | 6/2001 | Coelho | 600/585 |
| 6,290,674 B1 | 9/2001 | Roue et al. | |
| 6,328,727 B1 | 12/2001 | Frazier et al. | |
| 6,358,197 B1 | 3/2002 | Silverman et al. | |
| 6,419,669 B1 | 7/2002 | Frazier et al. | |
| 6,423,087 B1 | 7/2002 | Sawada | |
| 6,491,707 B2 | 12/2002 | Makower et al. | |
| 6,572,629 B2 | 6/2003 | Kalloo et al. | |
| 6,592,559 B1 | 7/2003 | Pakter et al. | |
| 6,638,275 B1 * | 10/2003 | McGaffigan et al. | 606/41 |
| 6,641,557 B1 | 11/2003 | Frazier et al. | |
| 6,699,263 B2 | 3/2004 | Cope | |
| 6,712,804 B2 | 3/2004 | Roue et al. | |
| 6,746,472 B2 | 6/2004 | Frazier et al. | |
| 7,025,756 B2 | 4/2006 | Frazier et al. | |
| 7,056,325 B1 | 6/2006 | Makower et al. | |
| 7,087,073 B2 | 8/2006 | Bonutti | |
| 7,115,110 B2 | 10/2006 | Frazier et al. | |
| 7,217,279 B2 | 5/2007 | Reese | |
| 7,326,221 B2 | 2/2008 | Sakamoto et al. | |
| 7,390,329 B2 | 6/2008 | Westra et al. | |
| 7,416,554 B2 | 8/2008 | Lam et al. | |
| 7,431,694 B2 | 10/2008 | Stefanchik et al. | |
| 7,481,826 B2 | 1/2009 | Cichocki, Jr. | |
| 7,494,496 B2 | 2/2009 | Swain et al. | |
| 2001/0021855 A1 | 9/2001 | Levinson | |
| 2001/0039436 A1 | 11/2001 | Frazier et al. | |
| 2002/0188189 A1 * | 12/2002 | Belef et al. | 600/407 |
| 2003/0208209 A1 | 11/2003 | Gambale et al. | |
| 2004/0153074 A1 | 8/2004 | Bojarski et al. | |
| 2004/0186514 A1 | 9/2004 | Swain et al. | |
| 2005/0113851 A1 | 5/2005 | Swain et al. | |
| 2005/0154401 A1 | 7/2005 | Weldon et al. | |
| 2005/0234297 A1 * | 10/2005 | Devierre et al. | 600/153 |
| 2005/0240201 A1 | 10/2005 | Yeung | |
| 2005/0251165 A1 | 11/2005 | Vaughan et al. | |
| 2005/0251166 A1 | 11/2005 | Vaughan et al. | |
| 2005/0251177 A1 | 11/2005 | Saadat et al. | |
| 2005/0277945 A1 | 12/2005 | Saadat et al. | |
| 2005/0277981 A1 | 12/2005 | Maahs et al. | |
| 2006/0004409 A1 | 1/2006 | Nobis et al. | |
| 2006/0004410 A1 | 1/2006 | Nobis et al. | |
| 2006/0015006 A1 | 1/2006 | Laurence et al. | |
| 2006/0015125 A1 | 1/2006 | Swain | |
| 2006/0020274 A1 | 1/2006 | Ewers et al. | |
| 2006/0025654 A1 | 2/2006 | Suzuki et al. | |
| 2006/0025819 A1 | 2/2006 | Nobis et al. | |
| 2006/0190016 A1 | 8/2006 | Onuki et al. | |
| 2006/0206063 A1 | 9/2006 | Kagan et al. | |
| 2006/0207608 A1 | 9/2006 | Hirotsuka et al. | |
| 2006/0217762 A1 | 9/2006 | Maahs et al. | |
| 2006/0237022 A1 | 10/2006 | Chen et al. | |
| 2006/0237023 A1 | 10/2006 | Cox et al. | |
| 2006/0253144 A1 | 11/2006 | Mikkaichi et al. | |
| 2006/0270906 A1 | 11/2006 | Matsuno | |
| 2006/0271073 A1 | 11/2006 | Lam et al. | |
| 2006/0271101 A1 | 11/2006 | Saadat et al. | |
| 2007/0032820 A1 | 2/2007 | Chin-Chen et al. | |
| 2007/0038232 A1 | 2/2007 | Kraemer | |
| 2007/0073320 A1 * | 3/2007 | Mikkaichi et al. | 606/153 |
| 2007/0100375 A1 | 5/2007 | Mikkaichi et al. | |
| 2007/0100376 A1 | 5/2007 | Mikkaichi et al. | |
| 2007/0112362 A1 | 5/2007 | Mikkaichi et al. | |
| 2007/0123840 A1 | 5/2007 | Cox | |
| 2007/0191886 A1 | 8/2007 | Dejima et al. | |
| 2007/0219411 A1 | 9/2007 | Dejima et al. | |
| 2007/0265647 A1 | 11/2007 | Bonnette et al. | |
| 2007/0270752 A1 | 11/2007 | LaBombard | |
| 2007/0270889 A1 | 11/2007 | Conlon et al. | |
| 2007/0276424 A1 | 11/2007 | Mikkaichi et al. | |
| 2008/0009888 A1 | 1/2008 | Ewers et al. | |
| 2008/0086153 A1 | 4/2008 | Sakamoto et al. | |
| 2008/0097152 A1 | 4/2008 | Stefanchik et al. | |
| 2008/0177304 A1 | 7/2008 | Westra et al. | |
| 2008/0183035 A1 | 7/2008 | Vakharia et al. | |
| 2008/0185752 A1 | 8/2008 | Cerwin et al. | |
| 2008/0200930 A1 | 8/2008 | Saadat et al. | |
| 2008/0208161 A1 | 8/2008 | Kaji et al. | |
| 2008/0208214 A1 | 8/2008 | Sato et al. | |
| 2008/0208218 A1 | 8/2008 | Shiono | |
| 2008/0208219 A1 | 8/2008 | Suzuki | |
| 2008/0208220 A1 | 8/2008 | Shiono et al. | |
| 2008/0221619 A1 | 9/2008 | Spivey et al. | |
| 2008/0228203 A1 | 9/2008 | Bell et al. | |
| 2008/0243148 A1 | 10/2008 | Mikkaichi et al. | |
| 2008/0255422 A1 | 10/2008 | Kondoh et al. | |
| 2008/0255423 A1 | 10/2008 | Kondo et al. | |
| 2008/0262525 A1 | 10/2008 | Chang et al. | |
| 2008/0275297 A1 | 11/2008 | Bakos et al. | |
| 2008/0300547 A1 | 12/2008 | Bakos | |
| 2008/0319257 A1 | 12/2008 | Sato et al. | |
| 2009/0005638 A1 | 1/2009 | Zwolinski | |
| 2009/0005800 A1 | 1/2009 | Franer et al. | |
| 2009/0018552 A1 | 1/2009 | Lam et al. | |
| 2009/0018602 A1 | 1/2009 | Mitelberg et al. | |
| 2009/0088780 A1 | 4/2009 | Shiono et al. | |
| 2009/0088797 A1 | 4/2009 | Crombie et al. | |
| 2009/0125039 A1 | 5/2009 | Mikkaichi et al. | |
| 2009/0149714 A1 | 6/2009 | Bonadio | |
| 2010/0036198 A1 * | 2/2010 | Tacchino et al. | 600/106 |

FOREIGN PATENT DOCUMENTS

| | | | | |
|---|---|---|---|---|
| JP | 2006223358 A * | 8/2006 | | A61B 1/00 |
| WO | WO 99/12480 | 3/1999 | | |
| WO | WO 2006/109377 | 10/2006 | | |

OTHER PUBLICATIONS

International Search Report; PCT/US2008/077382 (Dec. 18, 2008).
International Search Report; PCT/US2008/085157 (May 12, 2009).

* cited by examiner

MEDICAL DEVICES, SYSTEMS AND METHODS FOR CLOSING PERFORATIONS

CROSS-REFERENCE TO RELATED APPLICATIONS

This application claims the benefit of U.S. Provisional Application Ser. No. 60/940,246 filed on May 25, 2007, entitled "MEDICAL DEVICES, SYSTEMS AND METHODS FOR CLOSING PERFORATIONS," the entire contents of which are incorporated herein by reference.

FIELD OF THE INVENTION

The present invention relates generally to medical devices, systems, and methods for closing perforations in tissue.

BACKGROUND OF THE INVENTION

Perforations in the walls of internal organs and vessels may be naturally occurring, or formed intentionally or unintentionally. In order to permanently close these perforations and allow the tissue to properly heal, numerous tissue fixation devices and methods have been developed employing sutures, adhesives, clips, staples and the like. One class of such devices is commonly referred to as T-anchors, also known as tissue anchors or visceral anchors. An exemplary tissue anchor is disclosed in U.S. Pat. No. 5,123,914, the entire contents of which are incorporated by reference herein. Such tissue anchors have been very successful in medical procedures requiring visceral wall mobilization or wall apposition.

Tissue anchors have also been successfully used in closing perforations, but are not without their drawbacks. For example, when a series of anchors are placed around a perforation, each individual anchor is manually placed in sequence. This can be time consuming, and can result in uneven spacing of the anchors around the perforation. It can therefore be difficult to ensure proper approximation of the tissue around the perforation and complete closure thereof. This is especially critical within the gastrointestinal tract, where the travel of bacteria laden fluids outside of the tract may cause unwanted and sometimes deadly infection.

BRIEF SUMMARY OF THE INVENTION

The present invention provides medical devices, systems and methods for placing tissue fixation devices that are easy to employ, reduce procedure time, and improve spacing of the tissue fixation devices. One embodiment of a medical device, constructed in accordance with the teachings of the present invention, includes a plurality of elongate delivery devices, a plurality of elongate tubes, and a distal tip. Preferably the delivery devices are needles, although other devices may be used for delivering tissue fixation devices. Each delivery device defines a delivery lumen sized to receive a tissue fixation device. The plurality of elongate tubes extend generally parallel to a longitudinal axis, and each tube defines a tube lumen sized to receive one of the delivery devices. Each tube lumen has a distal port. The distal tip is connected to the plurality of elongate tubes and defines a guide surface positioned distally of the distal ports. The guide surface is structured to redirect the plurality of delivery devices radially outwardly as the plurality of delivery devices are distally translated through the tube lumens and the distal ports of the plurality of elongate tubes.

According to more detailed aspects of the medical device, the guide surface slopes radially outwardly, and preferably is curved. The guide surface redirects the plurality of delivery devices in a direction angled relative to the longitudinal axis, preferably angled in the range of 10 to 60 degrees, and most preferably about 30 degrees. The distal tip defines a hub having a plurality of pockets sized to receive the plurality of elongate tubes. An end surface of the distal tip is atraumatically shaped. Preferably, the delivery devices are puncture needles, and the tissue fixation devices are tissue anchors.

A medical system for placing tissue fixation devices in bodily tissues is also provided. According to one embodiment of the medical system, the system includes a plurality of elongate delivery devices, a plurality of elongate tubes, a distal tip, and an endoscope. The plurality of delivery devices each define a delivery lumen sized to receive a tissue fixation device. The plurality of elongate tubes extend generally parallel to a longitudinal axis and each tube defines a tube lumen sized to receive one of the plurality of delivery devices. Each tube lumen defines a distal port. A distal tip is connected to the plurality of elongate tubes and defines a guide surface positioned distally of the distal ports and extending radially outwardly. The distal tip defines a passageway. The endoscope is selectively attachable to the distal tip, and the passageway is sized to receive a distal end of the endoscope therein.

According to more detailed aspects of the medical system, the endoscope is loosely press fit within the passageway of the distal tip. The passageway defines an inner surface, and the inner surface is positioned to frictionally engage the endoscope. The plurality of tubes extend along an outer surface of the endoscope. The guide surface is structured to redirect the plurality of delivery devices radially outwardly as the plurality of delivery devices are distally translated through the tube lumens and the distal ports of the plurality of elongate tubes.

A method of placing tissue fixation devices in bodily tissue of a patient is also provided in accordance with the teachings of the present invention. One embodiment of the method includes providing a medical system comprising a medical device and an endoscope, such as those previously described. The endoscope is attached to the medical device, and the medical system is introduced through a bodily lumen of the patient to a position proximate the bodily tissue. The plurality of delivery devices are translated distally through the plurality of tubes such that the plurality of delivery devices engage the guide surface and deflect radially outwardly. The plurality of delivery devices are positioned proximate the bodily tissue. The plurality of tissue fixation devices are delivered through the plurality of delivery devices to a position engaged with the bodily tissue.

According to more detailed aspects of the method, the plurality of delivery devices are retracted into the plurality of tubes. A cutting instrument may be passed through an accessory channel of the endoscope and used to form an opening in the bodily tissue. The step of forming the opening is preferably performed after the step of positioning the plurality of delivery devices proximate the bodily tissue, and most preferably after the step of delivering the plurality of tissue fixation devices. The method also includes adjusting the position of the medical system relative to the bodily tissue prior to the step of passing the plurality of delivery devices through the bodily tissue. In this manner, the spacing of the tissue fixation devices may be easily controlled. The endoscope and medical device may be retracted, and the endoscope or other medical instrument may be reintroduced through the bodily lumen and through the opening in the bodily tissue. Finally, the plurality of tissue fixation devices are connected together, such as by tying one or more sutures which are attached to the tissue fixation devices.

DETAILED DESCRIPTION OF THE INVENTION

Figure 1:
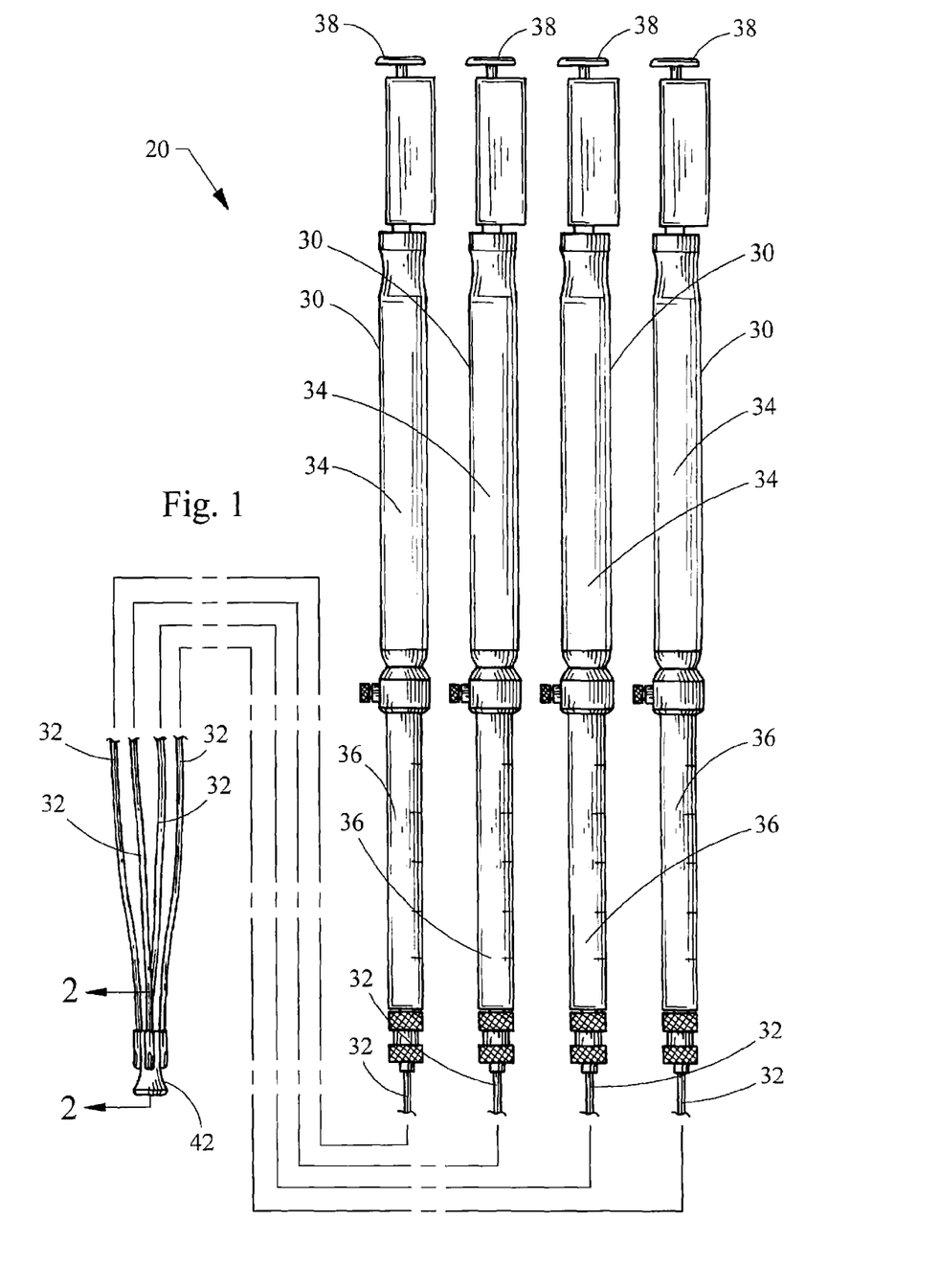
FIG. 1 is a plan view, partially cut-away, showing a medical device constructed in accordance with the teachings of the present invention.
Figure 2:
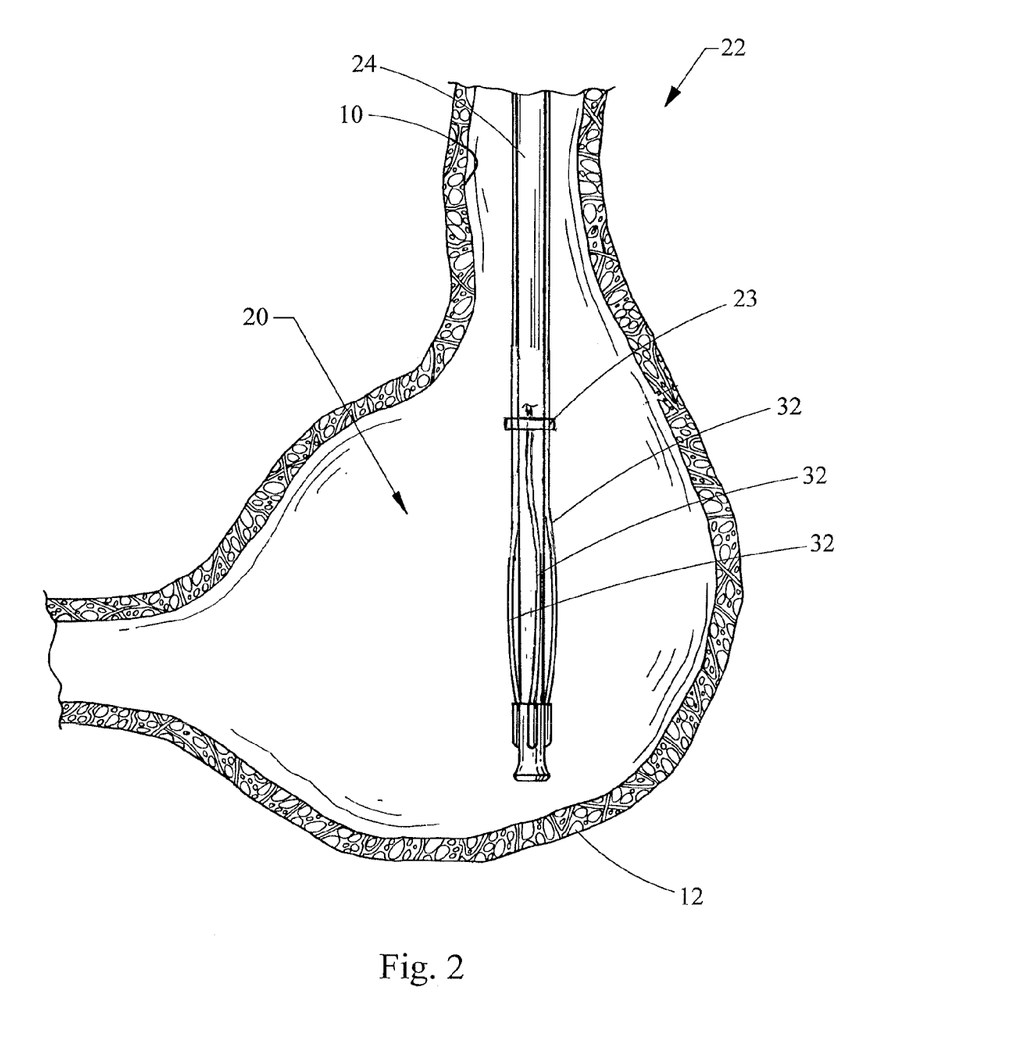
FIG. 2 is a front view, partially in cross-section, showing a medical system including the medical device depicted in FIG. 1, constructed in accordance with the teachings of the present invention.

Turning now to the figures, FIG. 1 depicts a medical device 20 constructed in accordance with the teachings of the present invention. As shown in FIG. 2, the medical device 20 also forms part of a medical system 22, which includes the medical device 20 and an endoscope 24. Generally, the medical device 20 is selectively attachable to the endoscope 24, and the medical system 22 may be traversed through a bodily lumen of a patient to a desired location for performing procedures within the body, such as at a particular bodily wall or tissue. As depicted in FIG. 2, the bodily lumen may be the esophagus 10 while the bodily tissue may be the gastric wall 12, although the medical system 22 may be used with any bodily lumen and tissue, as will be understood by those skilled in the art.

Turning back to FIG. 1, the medical device 20 generally includes a plurality of puncture needles 30 and a plurality of tubes 32. The plurality of needles 30 have at their proximal end a plurality of needle housings 34, while the proximal end of the plurality of tubes 32 includes a plurality of tube housings 36. As is known to those skilled in the art, the relative positions of the needle housings 34 and the tube housings 36 control the relative positions of the needles 30 within the protective tubes 32. In this manner, the needles 30 may be operated to project from a distal end of the tubes 32, or operated to be retracted within the tubes 32, as will be described in more detail hereinbelow. The proximal end of the medical device 20 also includes a plurality of plungers 38 which are connected to stylets 40 (FIG. 3) that extend through the plurality of needles 30. The stylets 40 (operated via their plungers 38) are used to push tissue fixation devices such as tissue anchors 54 (FIG. 3) out from the distal ends of the needles 30.

Figure 3:
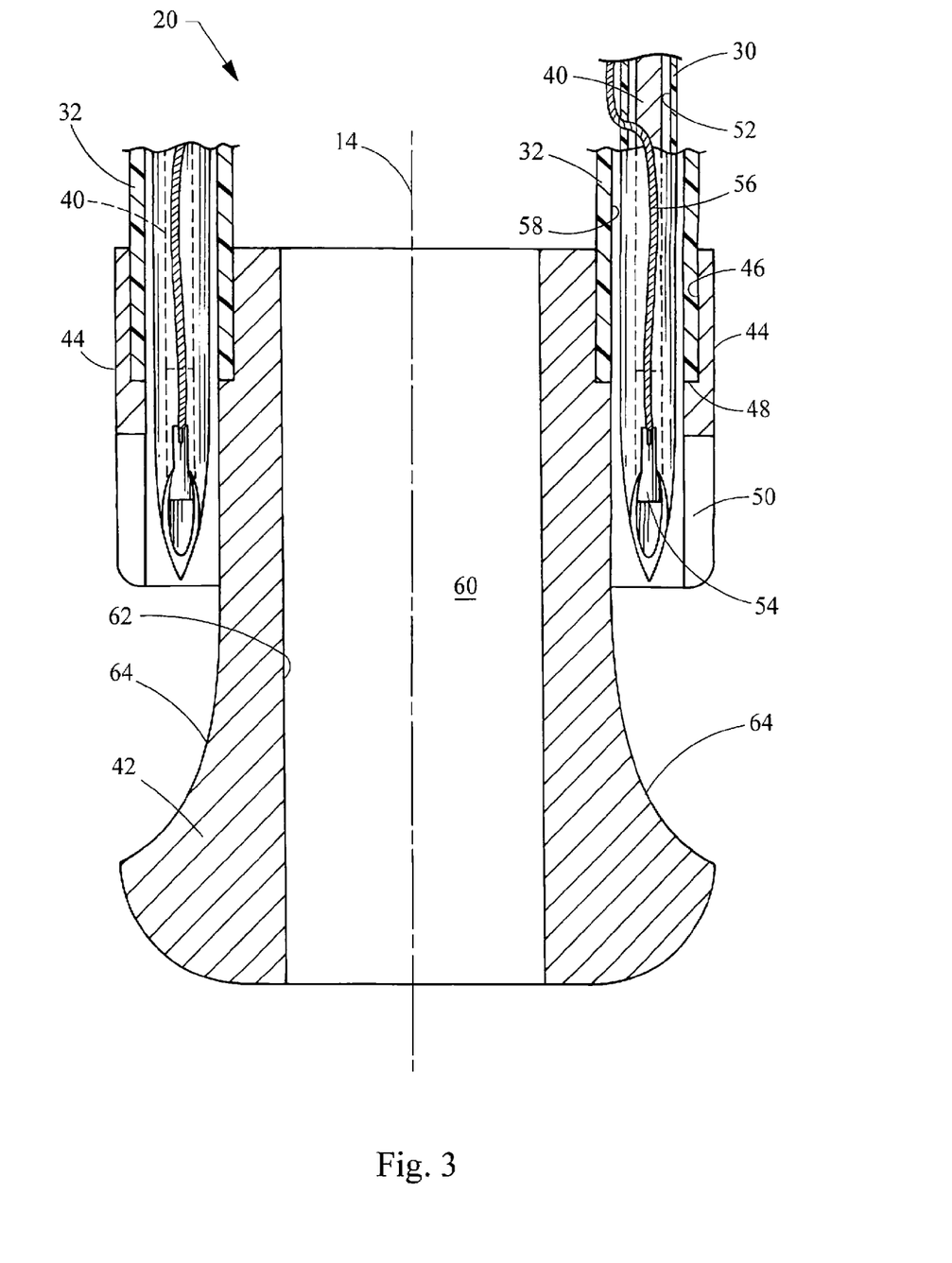
FIG. 3 is an enlarged cross-sectional view, partially cut away, of the distal end of the medical device depicted in FIG. 1.

With reference to FIGS. 1 and 3, the plurality of tubes 32 are connected to a distal tip 42 at the distal end of the tubes 32. The distal tip 42 generally includes a plurality of hubs 44 defining a plurality of pockets 46 for receiving the plurality of tubes 32, as best seen in FIG. 3. The hubs 44 could be a single hub having a plurality of pockets 46, or as shown in FIG. 2, individual and discreet hubs 44 may be designed to define the plurality of pockets 46. Each hub 44 defines a shoulder 48 at the bottom of the pocket 46 for abutting a distal end of each tube 32. The distal tip 42 and plurality of tubes 32 may be interconnected through frictional engagement, adhesives, welding, soldering or any other well known means for connecting two structures. The hubs 44 define distal ports 55 through which the plurality of needles 30 extend and are exposed for placement through the bodily tissue 12. It will be recognized by those skilled in the art that the distal tip 42 may simply have the plurality of tubes 32 attached to its exterior surface, thereby eliminating the hub or hubs 44 and their pockets 46. In this case, the plurality of tubes 32 themselves would define the distal ports 55 though which the needles 30 can exit. The distal ports 55 are circumferentially spaced about the distal tip 42. Preferably the distal ports 55 are equidistantly spaced to provide for delivery of the tissue anchors 54 in a generally equidistantly spaced configuration, although different spacings may be designed, such as to match the shape of the perforation 16 (FIG. 7) in the tissue 12, which can be elongated or otherwise uneven, rather than circular.

As also best seen in FIG. 3, the plurality of tubes 32 each define a tube lumen 58 which slideably receives the needles 30 therein. Similarly, the needles 30 each define a needle lumen 52 which is sized to receive the stylet 40. A distal end 31 of each needle 30 contains one or more tissue anchors 54 positioned within the needle lumen 52. The distal end 31 also includes a slot 33 through which the suture 56 passes. The suture 56 is connected to the tissue anchor 54 and is used to draw the perforation 16 (FIG. 7) closed, as is known in the art. It can be seen in FIG. 3 that the suture 56 extends proximally through the tube lumen 58 between the needle 30 and tube 32. It will also be recognized by those skilled in the art that the suture 56 could alternatively pass through the interior of the needle 30, i.e., through the needle lumen 52. The tissue anchors 54 may be pre-loaded within the needles 30, and likewise the needles may be pre-loaded within the plurality of tubes 32, although this is not necessary.

Notably, various types and designs of tissue anchors 54 may be employed in conjunction with the present invention, exemplary tissue anchors being disclosed in U.S. Pat. No. 5,123,914; and U.S. patent application Ser. No. 11/946,565. It will also be recognized that the medical device 20 and medical system 22 of the present invention may also be used in conjunction with other tissue fixation devices such as staples, an exemplary tissue staple and system being disclosed in U.S. Patent Application No. 60/956,580). The disclosures of all of the above-identified patents/applications are hereby incorporated by reference in their entireties. Accordingly, it will be seen that the plurality of puncture needles 30 can be replaced with other elongate delivery devices, such as delivery catheters for tissue staples, dependent upon the particular tissue fixation device.

Figure 4:
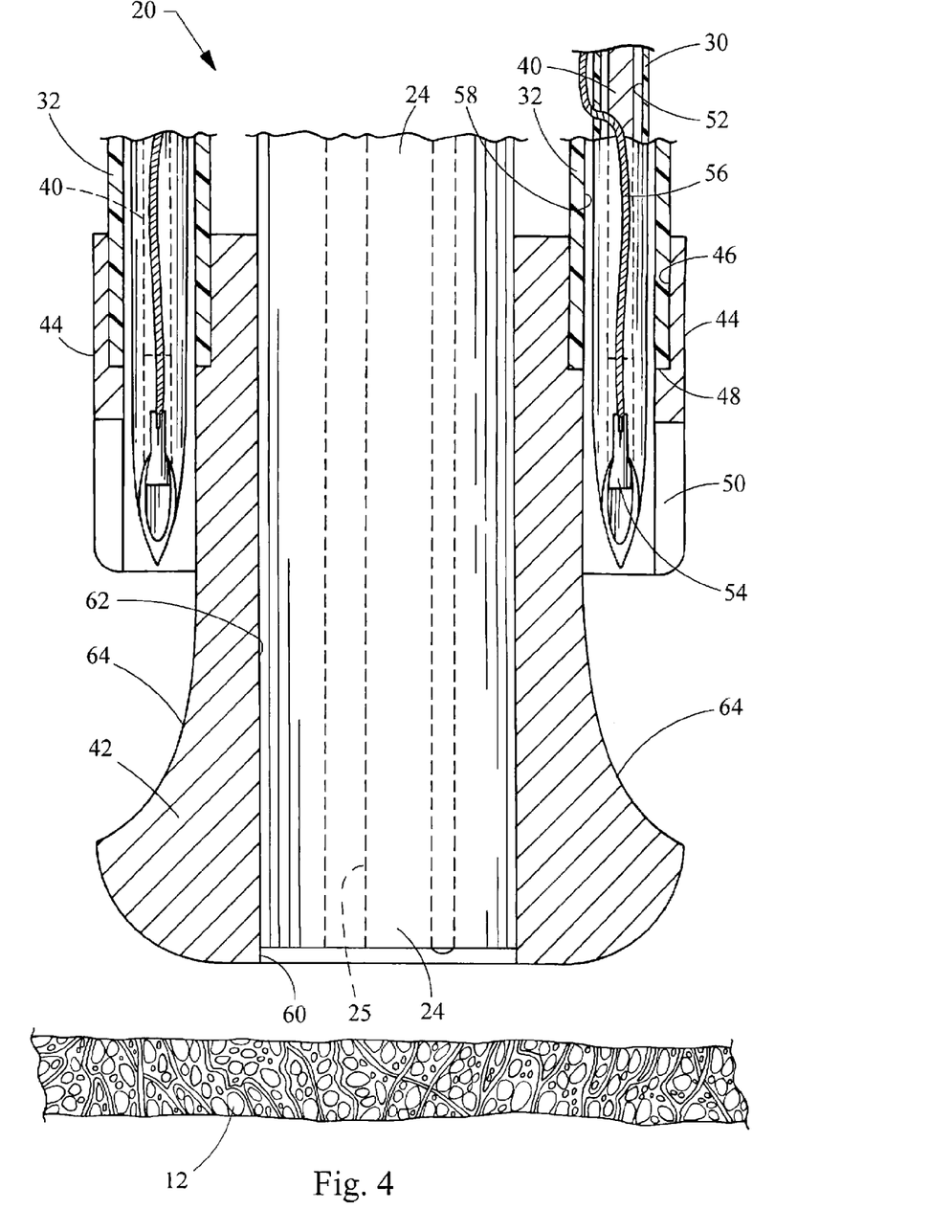
FIG. 4 is an enlarged cross-sectional view, partially cut away, of the distal end of the medical system depicted in FIG. 2.

As best seen in FIGS. 3 and 4, the distal tip 42 includes an interior passageway 60 defined by an interior wall 62. As shown in FIG. 4, the passageway 60 and interior wall 62 are sized to receive an endoscope therein for forming the medical system 22 of the present invention. In the depicted embodiment, the passageway 60 and wall 62 are sized to be loosely press-fit with the endoscope 24 such that they are selectively attachable, although it will be recognized by those skilled in the art that many different structures and means for selectively attaching the endoscope 24 to the medical device 20 may be employed. An end surface 66 of the distal tip is atraumatically shaped, i.e. rounded, such that the medical system 22 may be safely navigated through the patient's bodily lumens.

It can also be seen that the plurality of tubes 32 and needles 30 generally extend along a longitudinal axis 14 that is also shared by the distal tip 42. The plurality of tubes 32 are elongated and structured to extend longitudinally along the outer surface of the endoscope 24, as shown in FIG. 2. A band 23 or other structure may be used to connect the plurality of tubes 32 to the endoscope 24 at points along the length of the medical system 22, although such bands 23 or the like are not necessary to traverse the medical system 22 through the bodily lumen 10. It will also be recognized that the endoscope 24 can be integrally formed with the medical device 20, namely with the plurality of tubes 32 and distal tip 42. For example, the distal tip 42 and/or plurality of tubes 32 can be bonded to the endoscope 24, such as with an adhesive or using welding techniques.

Figure 5:
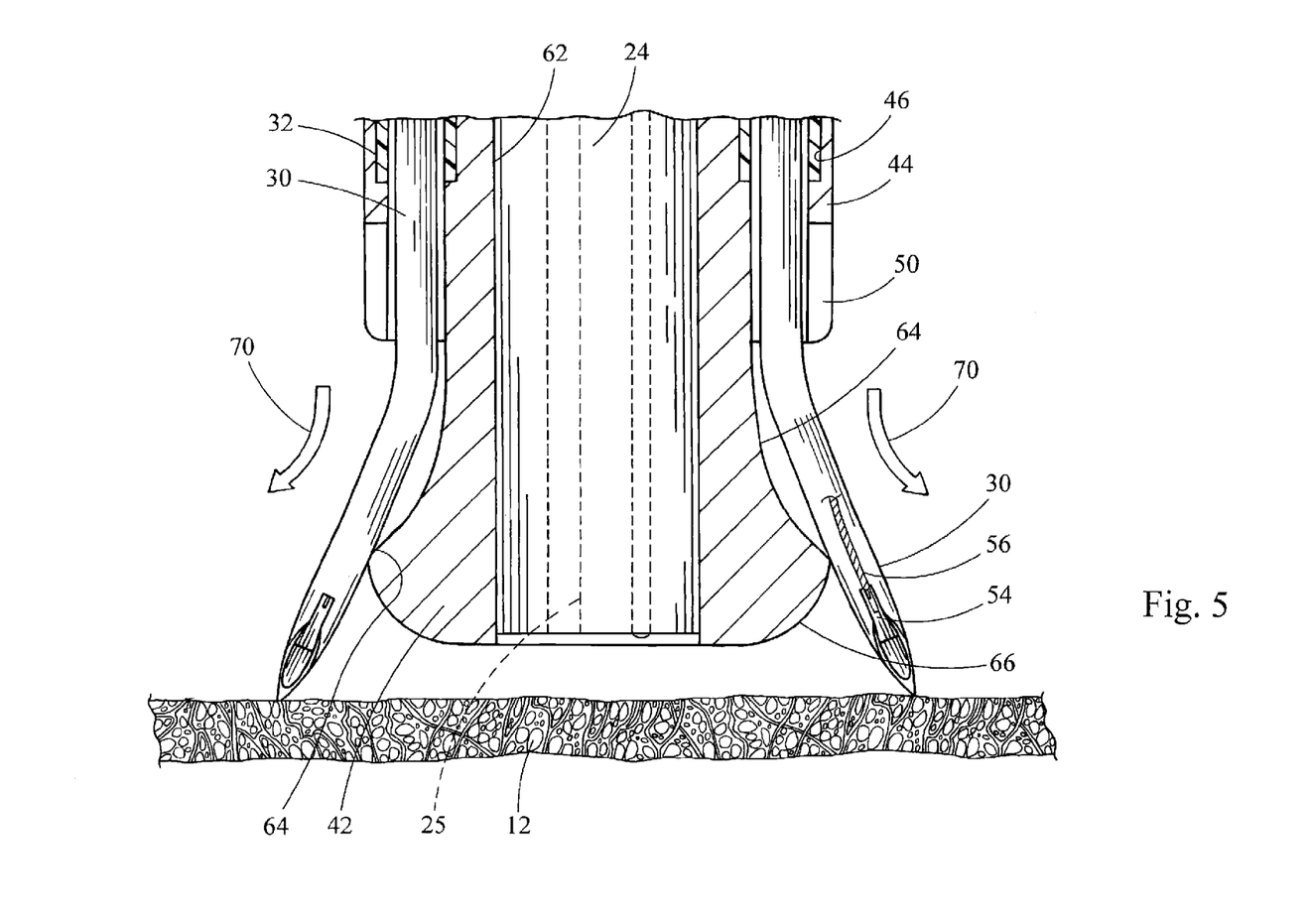
FIGS. 5, 6 and 7 are enlarged cross-sectional views similar to FIG. 4 showing operation of the medical system.
Figure 6:
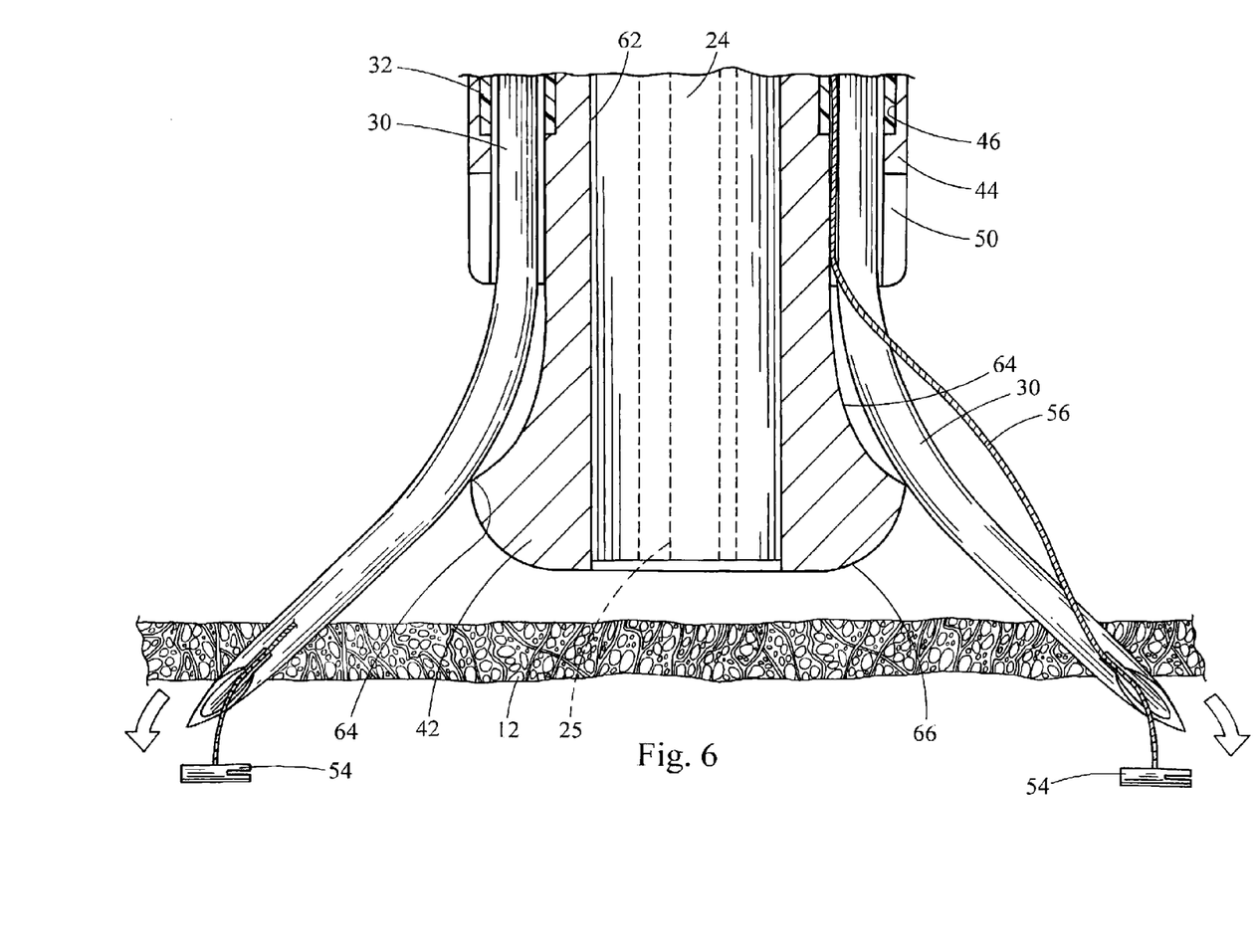

An outer surface of the distal tip 42 defines a guide surface 64. Generally, the guide surface 64 extends radially outwardly and is positioned distally of the distal port 55. As best seen in FIG. 5, as the plurality of needles 30 are distally translated relative to the plurality of tubes 32, the needles 30 project from the distal port 55 and engage the guide surface 64. The guide surface 64 extends radially outwardly and deflects the needles 30 radially outwardly, as indicated by arrow 70. As shown in FIG. 6, upon further translation in the distal direction, the needles 30 continue to flex and are directed radially outwardly. The hubs 44 define slots 50 that open radially, and the slots 50 provide increased range of movement to the needles 30 as they flex. In an embodiment where the plurality of tubes 32 are simply attached to the exterior surface of the distal tip 42 (i.e. without the hub 44 and pockets 46) these slots 50 may be formed in the tubes 32 themselves. As such, the needles 30 enter the slots 50 defined by the hub 44 and pockets 46, thereby permitting greater range of movement and preventing excessive flexing or bending of the needles 30.

Accordingly, the distal tip 42 and its guiding surface 64 move each of the needles 30 radially outwardly away from each other and away from the longitudinal axis 14. While the figures have depicted the guide surface 64 as curved, and generally a bell-shaped curve, it will be recognized by those skilled in the art that the guiding surface 64 may take many different curvatures, or can even be flat, such as in a conical or pyramidal shape (i.e. flat in the longitudinal direction). Further, the outer diameter of the distal tip 42 at its peak 65 may also be increased or decreased to increase or decrease the amount of deflection of the plurality of needles 30. The peaks 65 are preferably spaced radially outwardly of the distal ports 50. Preferably, the distal tip 42 and its guiding surface 64 are structured to cause the needles 30 to be passed through the tissue 12 at an angle of about 10 to 60 degrees relative to the longitudinal axis 14. Most preferably, the needles 30 are at an angle of about 30 degrees relative to the longitudinal axis 14. Further, the needles 30 are in paths that are circumferentially spaced apart, and preferably equidistantly spaced apart, thereby greatly improving the spacing of the tissue anchors 54 around a perforation 16 (FIG. 7) and improving perforation closure.

A method for placing tissue fixation devices in bodily tissue 12 of a patient will now be described with reference to FIGS. 2 and 5-7. A medical system 20 is provided, such as the medical device 20 and endoscope 24 as previously discussed. The endoscope 24 is attached to the medical device 20, namely by placing the distal end of the endoscope 24 into the interior passageway 60 of the distal tip 42. The medical system 20 is introduced through a bodily lumen 10 of the patient to a position proximate the bodily tissue 12, as shown in FIG. 2. The plurality of puncture needles 30 are translated distally through the plurality of tubes 32 such that the plurality of needles 30 engage the guide surface 64 and deflect radially outwardly, as shown in FIG. 5 and indicated by arrow 70. As shown in FIG. 6, the plurality of puncture needles 30 are passed through the bodily tissue 12. This may occur sequentially or simultaneously. It will be recognized by those skilled in the art that because the distance between each of the needles 30 increases in the longitudinal direction (i.e. the more distal the greater the spacing), the medical system 22 and its distal tip 42 may be placed closer to the tissue 12 to bring the placement sites closer together, or the medical system 22 may be moved further away from the tissue 12 to increase the distance between the placement sites. In embodiments where other types of tissue fixation devices and delivery devices are employed (e.g. a visceral staple and delivery catheter, respectively) the delivery device need only be positioned proximate the tissue 12, and need not pass through the tissue 12.

Figure 7:
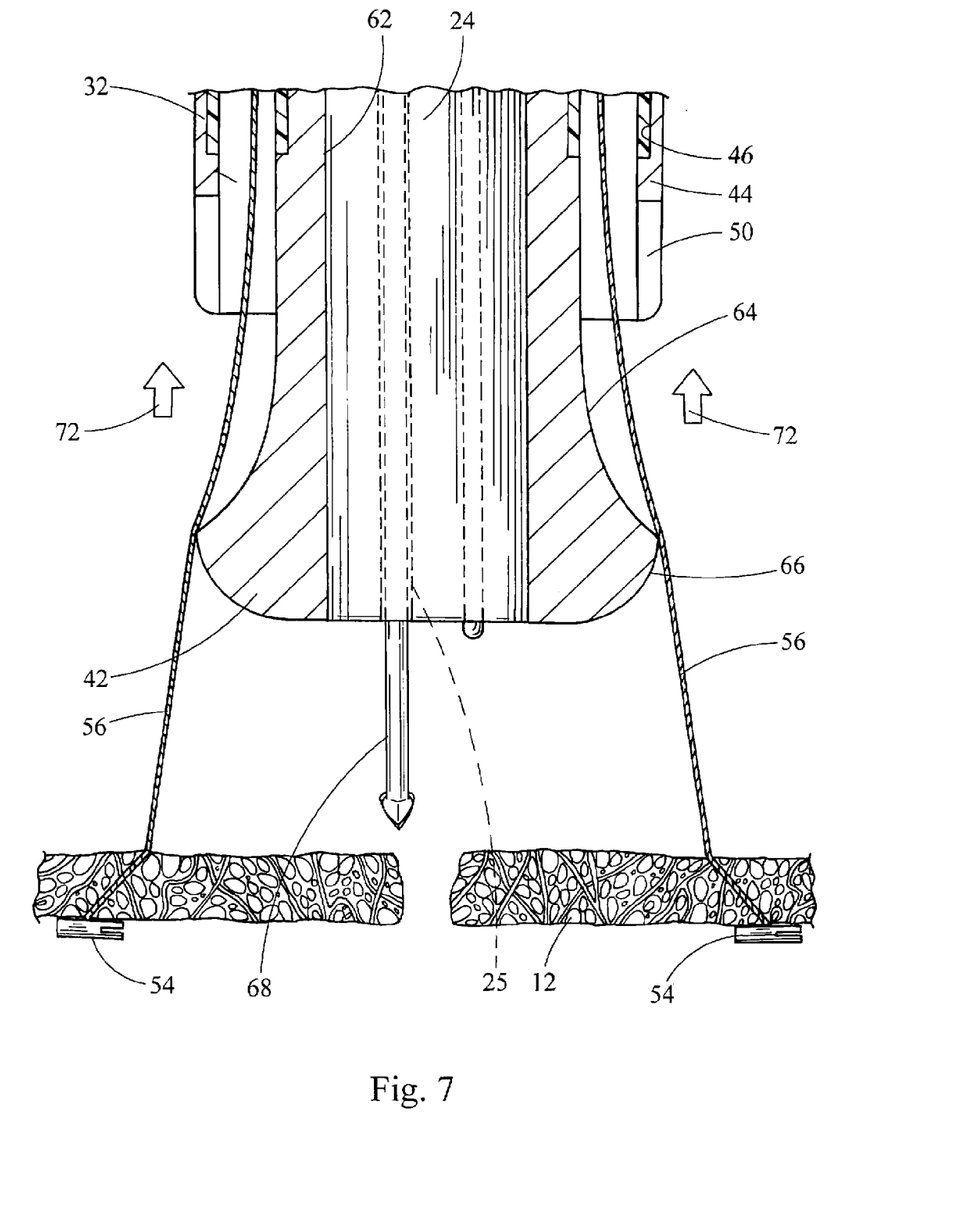

Once the plurality of puncture needles 30 have been passed through the bodily tissue 12, as shown in FIG. 6, the plurality of tissue anchors 54 are delivered to a position on the distal side of the bodily tissue 12. In the depicted embodiment, the tissue anchors 54 are connected to suture 56, and the anchors 54 are ejected from the distal end of the needles 30 through translation of the stylets 40 via depression of the plungers 38 (FIG. 1). As shown in FIG. 7 and indicated by arrow 72, the plurality of puncture needles 30 are then retracted into the plurality of tubes 30, leaving the tissue anchors 54 in place.

If desired, a cutting instrument 68 may then be delivered through the accessory channel 25 of the endoscope 24, and used to form an opening 16 in the tissue 12. Preferably, the cutting tool 68 is an electrosurgical cutting instrument, although it will be recognized by those skilled in the art that any type of cutting instrument or device may be employed. Preferably, the step of forming the opening 16 is performed after the step of translating the puncture needles 30 and most preferably after delivering the plurality of tissue anchors 54, thereby reducing the potential for the tissue 12 to deflect or move when placing the tissue anchors 54. However, the plurality of tissue anchors 54 or other tissue fixation devices may be delivered after the opening 16 has already been formed in the tissue 12. In either case, the tissue 12 (and sometimes the opening 16) is preferably visualized using the endoscope 24 prior to placing the plurality of puncture needles 30 through the bodily tissue 12.

The medical system 22 may be retracted through the bodily lumen 10, and the endoscope 24 may be detached from the medical device 20. If desired, the endoscope 24 may then be reintroduced through the bodily lumen 10 and through the opening 16 in the bodily tissue 12. As such, various procedures may be employed with, or in conjunction with, the endoscope 24 on the distal side of the bodily tissue 12. It will also be recognized that various other medical devices may be passed through the bodily lumen 10 and through the opening 16 formed in the bodily tissue 12. When the procedure(s) on the distal side of the opening 16 are complete, the one or more sutures 56 attached to the tissue anchors 54 are connected together, such as by using a suture lock. Exemplary suture locks are disclosed in U.S. Patent Application Nos. 60/941, 086 and 60/956,575, the disclosures of which are incorporated herein by reference in their entirety. Through fixation of the sutures 56, the perforation 16 can be easily and securely closed.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for placing tissue fixation devices in bodily tissue, the medical device comprising:
   an endoscope having a distal end;
   a plurality of elongate delivery devices, each delivery device defining a delivery lumen sized to receive a tissue fixation device;
   a plurality of elongate tubes extending generally parallel to a longitudinal axis, each tube defining a tube lumen sized to slidably receive one of the plurality of delivery devices, each tube lumen ending proximate a distal end of each elongate tube, each delivery device sliding within its elongate tube independently of the other delivery devices;
   a distal tip selectively fixed on the distal end of the endoscope, the distal tip fixedly connected to the plurality of elongate tubes, the distal tip having an exterior surface defining a guide surface positioned distally of the distal end of the plurality of elongate tubes, the guide surface structured to redirect the plurality of delivery devices radially outwardly as the plurality of delivery devices are distally translated through the tube lumens and the distal ends of the plurality of elongate tubes; and
   a plurality of tissue fixation devices, wherein the plurality of delivery devices include a plurality of puncture needles, and wherein the plurality of tissue fixation devices include a plurality of tissue anchors.

2. The medical device of claim 1, wherein the guide surface extends radially outwardly to a peak, the peak being spaced radially outwardly of the distal ends of the plurality of elongate tubes.

3. The medical device of claim 1, wherein the entire guide surface is curved radially outwardly.

4. The medical device of claim 1, wherein the distal tip defines one or more hubs having a plurality of pockets sized to receive the plurality of tubes.

5. The medical device of claim 4, where each hub has a bore extending therethrough, proximal portions of the bores defining the pockets and distal portions of the bores defining distal ports, and wherein each hub defines a longitudinal slot in communication with the bore and opening radially, each longitudinal slot sized to receive one of the delivery devices therein.

6. The medical device of claim 5, wherein each hub defines a shoulder at a bottom of each pocket for abutting the distal end of each of the plurality of elongate tubes.

7. The medical device of claim 1, wherein the plurality of tubes extend along an outer surface of the endoscope.

8. The medical device of claim 1, further comprising at least one band pressing the plurality of tubes against the endoscope.

9. The medical device of claim 1, wherein the guide surface slopes radially outwardly.

10. The medical device of claim 1, wherein the guide surface redirects the plurality of delivery devices in a direction angled relative to the longitudinal axis.

11. The medical device of claim 10, wherein the guide surface redirects the plurality of delivery devices in a direction angled about 30 degrees relative to the longitudinal axis.

12. The medical device of claim 1, wherein the plurality of elongate tubes are equidistantly spaced circumferentially about the distal tip.

13. The medical device of claim 1, wherein the plurality of elongate tubes are directly fixed to the distal tip through frictional engagement, adhesives, welding or soldering.

14. The medical device of claim 1, wherein the guide surface does not restrict circumferential movement of the delivery devices.

15. The medical device of claim 1, wherein the entire guide surface is uncovered such that the plurality of elongate delivery devices may freely extend radially outwardly away from the guide surface.

16. The medical device of claim 1, wherein the entire guide surface curves radially outwardly.

17. The medical device of claim 1, wherein the distal tip defines one or more hubs having a plurality of pockets sized to receive the plurality of tubes.

18. The medical device of claim 17, where each hub has a bore extending therethrough, proximal portions of the bores defining the pockets and distal portions of the bores defining distal ports, and wherein each hub defines a longitudinal slot in communication with the bore and opening radially, each longitudinal slot sized to receive one of the delivery devices therein.

19. The medical device of claim 1, wherein the guide surface redirects the plurality of delivery devices in a direction angled about 30 degrees relative to the longitudinal axis.

* * * * *